United States Patent
Wu et al.

(10) Patent No.: US 7,087,808 B2
(45) Date of Patent: Aug. 8, 2006

(54) METHOD FOR EXPRESSING MULTIPLE RECOMBINANT PROTEINS IN MILK OF TRANSGENIC NON-HUMAN MAMMALS

(75) Inventors: Shinn Chih Wu, Miaoli (TW); Teng Kuei Cheng, Taipei (TW); Chuan Mu Chen, Taichung (TW); Shau Ping Lin, Taipei (TW); Chon Ho Yen, Taichung (TW); Ping Cheng Yang, Hsinchu (TW)

(73) Assignee: Animal Technology Institute Taiwan, Miaoli (TW)

( * ) Notice: Subject to any disclaimer, the term of this patent is extended or adjusted under 35 U.S.C. 154(b) by 0 days.

(21) Appl. No.: 10/790,720

(22) Filed: Mar. 3, 2004

(65) Prior Publication Data

US 2005/0114911 A1 May 26, 2005

(30) Foreign Application Priority Data

Nov. 20, 2003 (TW) .............................. 92132541 A

(51) Int. Cl.
- C12P 21/00 (2006.01)
- A01K 67/00 (2006.01)
- A01K 67/027 (2006.01)
- C12N 15/00 (2006.01)
- C07H 21/04 (2006.01)

(52) U.S. Cl. .............................. 800/4; 800/13; 800/17; 800/21; 800/22; 800/25; 435/320.1; 536/23.5

(58) Field of Classification Search .................... 800/4, 800/7, 13, 17, 21, 22, 25; 435/1.1, 320.1; 536/23.5

See application file for complete search history.

(56) References Cited

OTHER PUBLICATIONS

Palmer CA et al., "Transgenic mice expressing recombinant human protein C exhibit defects in lactation and impaired mammary gland development." Transgenic Res 12(3):283-292, 2003.*

Mercier et al. "The modification of milk protein composition through transgenesis: progress and problems," In: Transgenic Animals: Generation and use, Ed. Houdebine LM, Harwood Academic Publishers, The Netherlands pp. 473-482, 1997.*

Hammer et al. "Spontaneous inflammatory disease in transgenic rats expressing HLA-B27 and human B2m: an animal model of HLA-B27-associated human disorders." Cell 63:1099-1112, 1990.*

Cameron ER "Recent advances in transgenic technology." Molecular Biotechnology 7:253-265, 1997.*

Dyck et al. "Making recombinant proteins in animals—different systems, different applications." Trends in Biotechnology 2(9):394-399, 2003.*

Kappel et al., 1992, Current Opinion in Biotechnology, vol. 3, p. 548-553.*

Sigmund, C., Jun. 2000, Arterioscler. Thromb. Vasc. Biol., p. 1425-1429.*

* cited by examiner

Primary Examiner—Shin-Lin Chen
(74) Attorney, Agent, or Firm—Bacon & Thomas, PLLC

(57) ABSTRACT

The present invention discloses a method for expressing multiple recombinant proteins in transgenic non-human mammalian milk, characterized in which human clotting factor IX gene and porcine lactoferrin gene are transferred into the mammal by gene injection and embryonic implantation to obtain expression in the milk of transgenic mammal and its filial generation. The method of this invention can maintain the stable expression of multiple recombinant proteins in the transgenic mammal during lactation and stable expression amount proximate to that of the first generation in the offsprings of the transgenic non-human mammal.

14 Claims, 5 Drawing Sheets

METHOD FOR EXPRESSING MULTIPLE RECOMBINANT PROTEINS IN MILK OF TRANSGENIC NON-HUMAN MAMMALS

BACKGROUND OF THE INVENTION

1. Field of the Invention

The present invention discloses a method for expressing multiple recombinant proteins in the milk of transgenic non-human mammals, characterized in which human clotting factor IX gene and porcine lactoferrin gene are transferred into the mammal by gene injection and embryonic implantation to obtain expression in the milk of transgenic mammal and its offsprings.

2. Description of Related Art

In clinical medicine, there are many cases involving the inability of in-vivo synthesis of bioactive protein due to genetic defect. This kind of diseases is usually managed by direct replenishment with recombinant proteins. Human clotting factor IX (hFIX) is a single chain glycoprotein with a molecular weight of 55 kDa. This protein is synthesized in liver and secreted into blood stream after translational modification. The level of hFIX in normal human plasma is about 5 µg/ml. In the plasma of patients suffered from hemophilia B, hFIX is absent, hence causing abnormal clotting function. It is known that hFIX gene is located in the long arm of X chromosome. Thus hemophilia B is a sex-linked hereditary disease, prevalent in males with average incidence of 1/30,000 (Thompson, 1986). Presently hFIX used on hemophilia B patients come from purified human plasma which carries the risk of infection (e.g. hepatitis and AIDS). If hFIX gene and tissue-specific regulatory sequence, such as α-lactalbumin regulatory sequence, are to be constructed into a recombinant expression plasmid, and then applying gene transfer technology to produce transgenic animal, it is possible to extract large quantity of hFIX with bioactivity in the animal milk without the concern about viral infection. The technique of mass-producing hFIX in the mammary glands of transgenic animals will provide great benefit for hemophilia B patients.

Recombinant hFIX cDNA was first expressed in the liver of transgenic mouse (Choo et al., 1987). It has been demonstrated that transgenic mouse carrying recombinant hFIX through gene transfer could express the products of said recombinant gene in its liver, and the level of liver-secreted hFIX in its blood was seven folds the level in normal human plasma (Jallat et al., 1990). Those experiments also found that when the recombinant hFIX retains the intron sequence, the expression efficiency of transgene is markedly elevated. Clark et al. (1989) also constructed a recombinant gene containing β-lactoglobulin (BLG) promoter and hFIX cDNA with mammary-specific expression for gene transfer in sheep and found that the resulting transgenic sheep could express the bioactive products of hFIX gene, but the expression level was only 25 ng/ml. Van Cott et al. (1999) fused mouse whey acidic protein promoter with the structural gene of hFIX and then transferred the recombinant gene into porcine chromosome. The result showed that the expression of transgene in the mammary gland of transgenic sow reached as high as 0.2 mg/ml, but the hFIX gene expression stopped during lactation. Based on the study results described above, there is high commercial value in the R&D of mass producing recombinant hFIX using the mammary gland of transgenic animals. Still, there are several obstacles to be overcome. For example, the expression level of recombinant hFIX in the milk of transgenic animal, the inability to sustain expression until the end of lactation, and improving the health of swine after hFIX gene and other genes of additive effect are co-transferred into the swine. These are the goals current research endeavors are attempting to obtain.

SUMMARY OF THE INVENTION

In addressing the drawbacks of prior methods for expressing human clotting factor XI in the milk of transgenic animals, the present invention aims to provide a method for continuous expression of multiple recombinant proteins in the milk of transgenic non-human mammals, comprising the steps of: (a) constructing expression plasmid that carries multiple recombinant protein genes and can express in mammary glands; and (b) transferring said expression plasmid by means of gene injection and embryonic implantation to a non-human mammal so that said multiple recombinant proteins are expressed in the milk of said transgenic non-human mammal and continue to be expressed during the lactation of the mammal.

In the aforesaid step (a), alternately the multiple recombinant protein genes may be constructed on the same expression plasmid or respectively on different plasmids; in case of the latter, an additional step of mixing different expression plasmids needs to be added between step (a) and step (b).

The construct of aforesaid expression plasmid containing multiple recombinant protein genes consists of 5' regulatory sequence having expression specificity to mammary glands and capable of regulating recombinant protein genes to obtain continuous and stable gene expression in the non-human transgenic mammal during its lactation; and recombinant protein genes that are located behind the regulatory sequence and subject to its control in expression.

The aforesaid 5' regulatory sequence is bovine α-lactalbumin promoter (αLA).

The aforesaid transferred multiple recombinant protein genes may be passed onto offspring through sexual reproduction.

The aforesaid multiple recombinant protein genes may include human clotting factor IX gene and lactoferrin gene, and the mixture ratio of expression plasmid carrying human clotting factor IX gene and that carrying lactoferrin gene to be transferred to the non-human mammal is 1:1.

The expression level of human clotting factor IX in the milk of aforesaid transgenic non-human mammal can reach 200–500 µg/mL, and its activity can reach 90% of normal human plasma after purification.

The aforesaid transgenic non-human mammal produced utilizing the method of the present invention can express recombinant proteins continuously and stably during lactation. The aforesaid transgenic non-human mammal may be cow, sheep or swine, and preferably swine.

The aforesaid method for continuous expression of multiple recombinant proteins in the milk of non-human mammals can be further added with the steps below after step (b):

(c) collecting the aforesaid milk containing multiple recombinant proteins; and (d) isolating the aforesaid multiple recombinant proteins from the milk, so as to obtain multiple recombinant proteins from the milk of transgenic non-human mammal.

Another objective of the present invention is to provide a method for continuously expressing human clotting factor IX and porcine lactoferrin in the milk of transgenic non-human mammals, comprising the steps of: (a) constructing expression plasmid that carries human clotting factor IX gene and porcine lactoferrin gene and can express in mammary glands; and (b) transferring said expression plasmid carrying human clotting factor IX gene and porcine lactoferrin gene by means of gene injection and embryonic implantation to a non-human mammal so that said human clotting factor IX and porcine lactoferrin are expressed in the milk of said transgenic non-human mammal and continue to be expressed during the lactation of the mammal.

In the aforesaid step (a), alternately the human clotting factor IX gene and porcine lactoferrin gene may be constructed on the same expression plasmid or respectively on different plasmids; in case of the latter, an additional step of mixing different expression plasmids in the ratio of 1:1 needs to be added between step (a) and step (b).

The construct of aforesaid expression plasmid containing human clotting factor IX gene and porcine lactoferrin gene consists of at least 5' regulatory sequence having expression specificity to mammary glands and capable of regulating human clotting factor IX gene and/or porcine lactoferrin gene to obtain continuous and stable expression of the gene(s) in the transgenic mammal during its lactation; and human clotting factor IX gene and porcine lactoferrin gene that are located behind the regulatory sequence and subject to its control in expression.

The aforesaid 5' regulatory sequence is bovine α-lactalbumin promoter.

The aforesaid transferred human clotting factor IX gene and porcine lactoferrin gene may be passed onto offspring through sexual reproduction.

The expression level of human clotting factor IX in the milk of aforesaid transgenic non-human mammal can reach 200–500 μg/mL, and its activity can reach 90% of normal human plasma after purification.

The aforesaid transgenic non-human mammal produced using the method of the present invention can express recombinant proteins continuously and stably during lactation. The aforesaid transgenic non-human mammal may be cow, sheep or swine, and preferably swine.

The aforesaid method for continuous expression of human clotting factor IX and porcine lactoferrin in the milk of transgenic non-human mammals can be further added with the steps below after step (b):

(c) collecting the aforesaid milk containing human clotting factor IX and porcine lactoferrin; and (d) isolating human clotting factor IX or porcine lactoferrin from the milk, so as to obtain human clotting factor IX or porcine lactoferrin from the milk of transgenic non-human mammal.

DETAILED DESCRIPTION OF THE INVENTION

The present invention is further depicted in the illustration of examples, but the descriptions made in the examples should not be construed as a limitation on the actual application of the present invention.

The present invention discloses a method for expressing multiple recombinant proteins in the milk of transgenic non-human mammals, which may apply in the production of double-transgenic swine carrying both human clotting factor IX gene and exogenous porcine lactoferrin gene. In the milk secreted by such double-transgenic swine, there expresses not only human clotting factor IX, but also exogenous porcine lactoferrin, which can help boost the immunity and resistance of nursing offsprings, reducing their diarrhea condition and fighting inflammation. This exogenous porcine lactoferrin differs from endogenous lactoferrin in that the former is secreted continuously and stably throughout lactation, while the secretion of endogenous lactoferrin drops through the lactating period.

EXAMPLE 1

Producing Transgenic Swine Carrying Recombinant Porcine Lactoferrin Gene and Human Clotting Factor IX Gene Porcine lactoferrin (pLF) gene and human clotting factor IX (hFIX) gene are constructed respectively with bovine α-lactalbumin promoter (α LA) on expression plasmids. After mixing the aforesaid two constructs in equimolar ratio of 1:1, microinject the mixture into embryo and then carry out embryonic implantation to obtain two lines of double-transgenic swine. Collect the milk of said double-transgenic swine during lactation for later use in the quantitative and qualitative analysis of recombinant protein expression.

EXAMPLE 2

Figure 1:
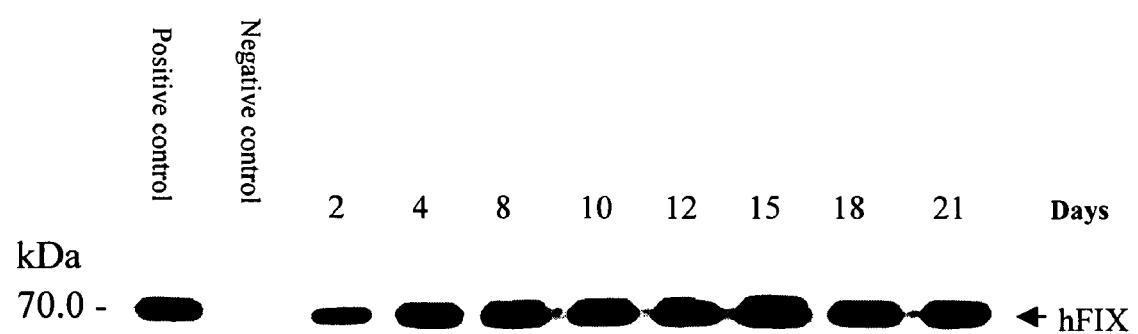
FIG. 1 shows the expression level of human clotting factor IX in the milk of the first-generation transgenic swine according to the present invention during lactation.

Analyzing the Expression of Recombinant Proteins in the Milk of First-Generation Transgenic Swine In this example, the milk collected in Example 1 is diluted 20 times and then subject to separation by SDS polyacrylamide gel electrophoresis (SDS-PAGE) and stained with Coomassie blue. Transfer the protein on electrophoretic gel to fibrous membrane to undergo western blot analysis. Use specific antibody to assay human clotting factor IX. The results as shown in FIG. 1 indicate the sustained stable expression of human clotting factor IX in the milk throughout the lactating period.

Figure 2:
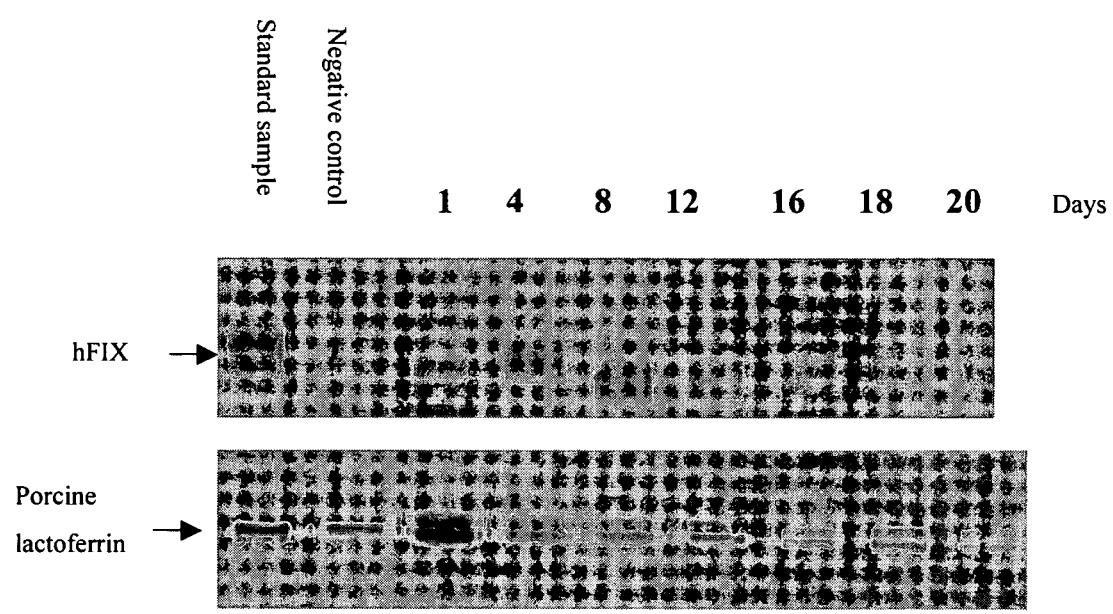
FIG. 2 shows the expression level of human clotting factor IX and porcine lactoferrin in the milk of the first-generation transgenic swine according to the present invention during lactation.

To confirm the expression of human clotting factor IX and porcine lactoferrin in the milk of first-generation transgenic swine, use the same steps as above, that is, after separating and staining the 20 times diluted milk using SDS-PAGE and Coomassie blue respectively, transfer the protein on electrophoretic gel to fibrous membrane to undergo western blot analysis. Use specific antibodies to assay human clotting factor IX and porcine lactoferrin. The results as shown in FIG. 2 indicate sustained stable expression levels of human clotting factor IX and porcine lactoferrin in the milk throughout the lactation, in which the level of the former in the sample is 50 ng, and that of the latter is 100 ng. The results of negative control showing the levels of human clotting factor IX and porcine lactoferrin in the milk of non-transgenic swine are provided for comparison purpose.

EXAMPLE 3

Figure 3:
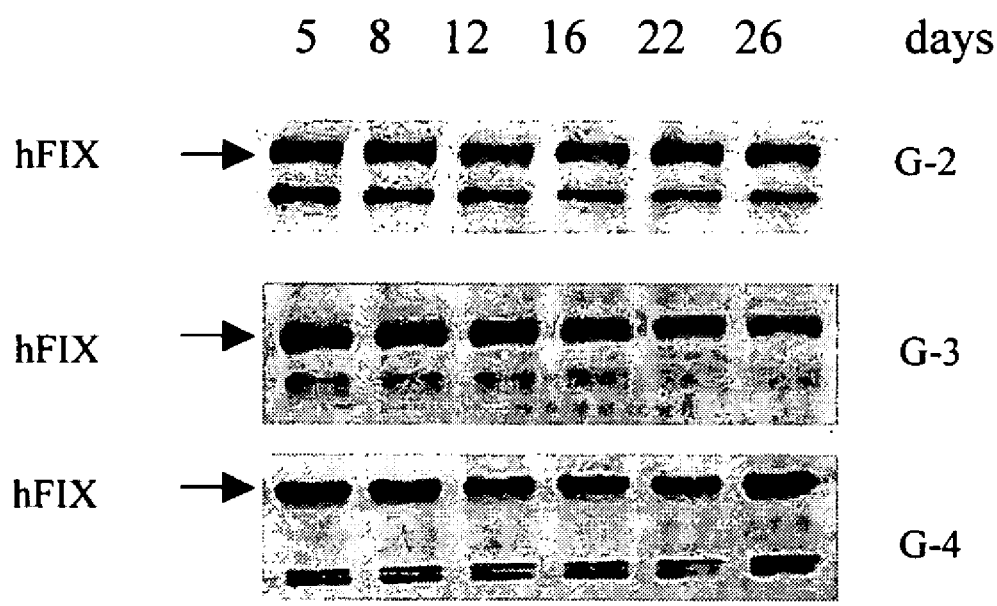
FIG. 3 shows the expression level of human clotting factor IX in the milk of the offsprings of transgenic swine according to the present invention during lactation.

Observing the Expression of Human Clotting Factor IX in the Milk of Offsprings of Transgenic Swine To confirm the expressions of human clotting factor IX in the milk of transgenic offsprings, the milks of the second generation (G-2), third generation (G-3) and fourth generation (G-4) offsprings of transgenic swine are collected. Carry out western blot analysis using the same steps as described in the example above and assay the level of human clotting factor IX with specific antibody. The results as shown in FIG. 3 find that the offsprings of transgenic swine continue expressing human clotting factor IX in their milk, and the expression level did not drop along with the duration of lactating period.

EXAMPLE 4

Figure 4:
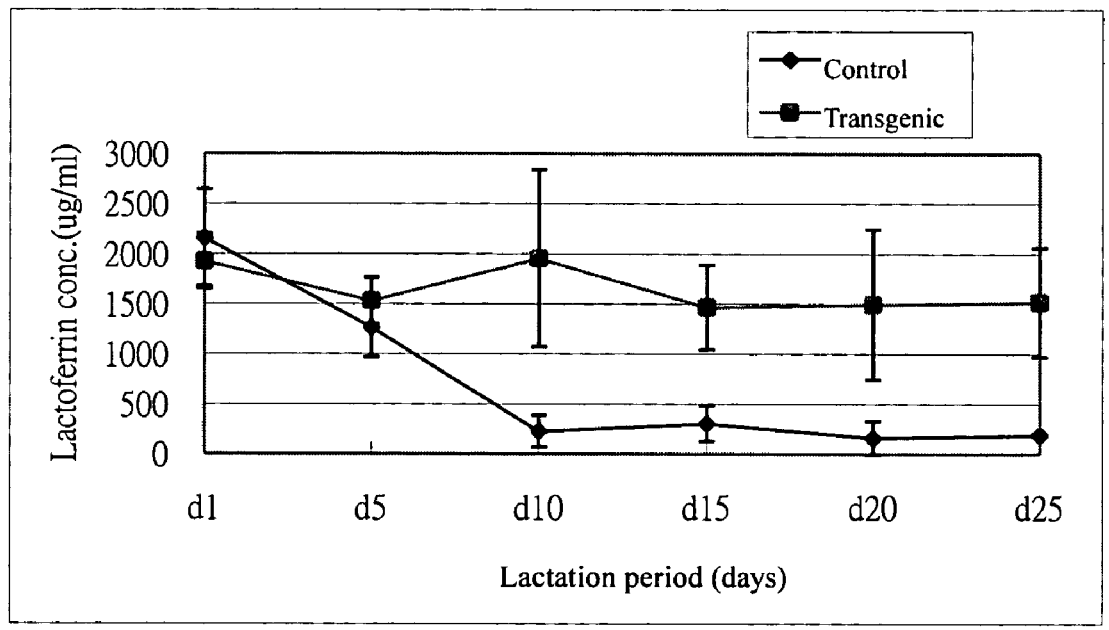
FIG. 4 shows the difference in the expression level of porcine lactoferrin in the milk of transgenic swine and non-transgenic swine.

Comparing the Difference Between the Expression Level of Porcine Lactoferrin in Transgenic and Non-Transgenic Swines Collect respectively the milk of transgenic swine and control (swine without gene transfer) during lactation and compare the expression of porcine lactoferrin in respective groups throughout the lactation. The results as shown in FIG. 4 indicate that porcine lactoferrin in the milk of the control dropped to very low level after the 10th day of lactation, while that of transgenic swine carrying the recombinant porcine lactoferrin gene showed high and stable level in comparison.

EXAMPLE 5

Figure 5:
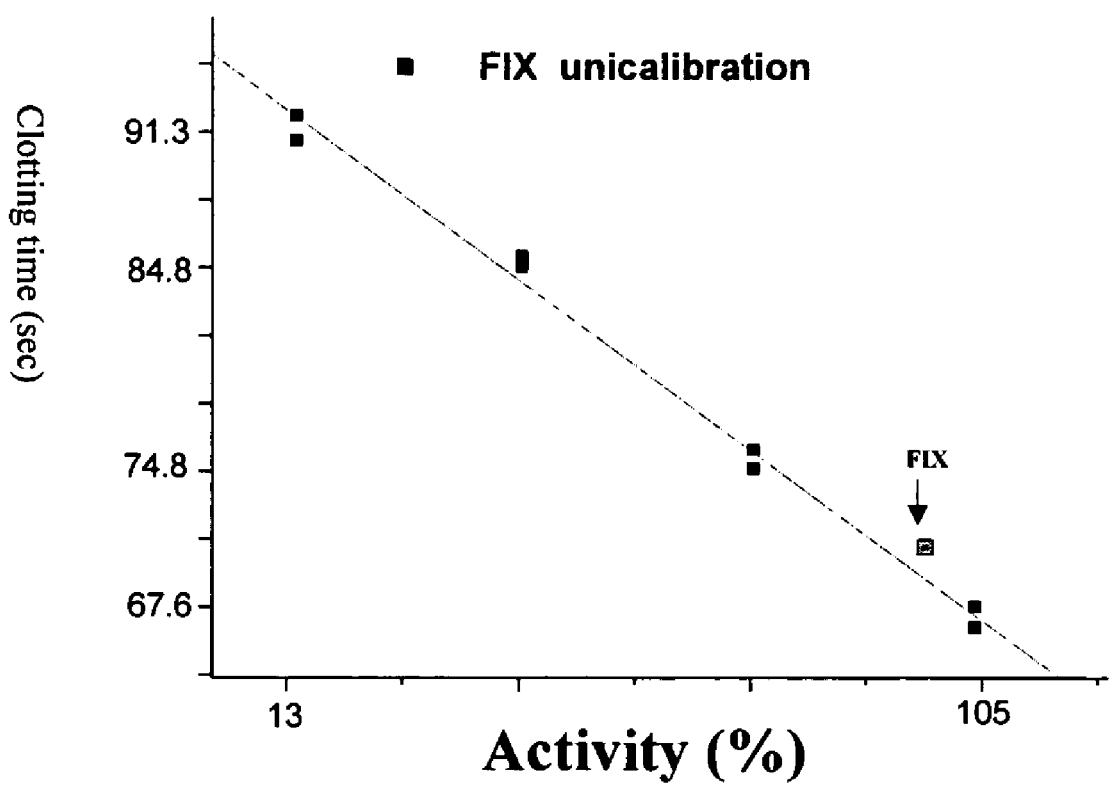
FIG. 5 depicts the activity of human clotting factor IX in the milk of transgenic swine according to the present invention.

Measuring the Activity of Human Clotting Factor IX in the Milk of Transgenic Swine The content of human clotting factor IX in per milliliter of porcine milk collected ranged from 200~500 µg, which is 40~100 times the level in normal human plasma (5 µg/ml) and was maintained at a stable level throughout the 28 days of lactation. The clotting activity (%) of the whole milk as analyzed by APTT was 14.18±2.45 (see Table 1), and may reach 90% of normal human plasma after purification (see FIG. 5).

TABLE 1

| Source of human clotting factor IX | Number of animals | Level of human clotting factor IX in milk | % clotting activity |
|---|---|---|---|
| Transgenic swine (whole milk) | 16 | 408.34 ± 55.0 | 14.18 ± 2.45 |
| Control swine (whole milk) | 3 | 0 | 0 |

The method disclosed in the present invention can successfully transfer two or more recombinant genes into swines, and the transgenes can express large quantity of protein continuously and stably throughout the lactating period of the swine. In comparison with prior transgenic technology where the expression of recombinant protein tends to drop significantly or even stops into the 11th day of lactating period, this invention shows non-obviousness.

Moreover, the offsprings of transgenic mammal according to this invention also carry the transgene, and the expression level of the recombinant genes is comparable to that in the first generation, which further illustrate the advantage of the present invention.

All modifications and alterations made by those familiar with the skill without departing from the spirits of the invention and appended claims shall remain within the protected scope and claims of the invention.

What is claimed is:

1. A method for producing a transgenic swine whose somatic and germ cells comprise transgenes, comprising the steps of:
   (a) constructing (i) an expression plasmid that comprises two transgenes wherein DNA sequences of said transgenes encode human clotting factor IX (hFIX) and porcine lactoferrin, respectively, wherein both transgenes are operably linked to a mammary gland specific promoter, or (ii) two expression transgenes, wherein one comprises a DNA sequence of transgene encoding human clotting factor IX (hFIX) operably linked to a mammary gland specific promoter, the other comprises a DNA sequence encoding porcine lactoferrin operably linked to a mammary gland specific promoter and the ratio of said two expression transgenes is 1:1;
   (b) introducing said expression plasmid or transgenes into a swine embryo;
   (c) transplanting said embryo comprising said expression transgene or transgenes into a recipient; and
   (d) allowing said embryo to develop into a transgenic swine, wherein expression of said transgenes result in the production and secretion of hFIX and porcine lactoferrin on the mammary tissue of said swine.

2. The method according to claim 1, wherein two expression transgenes are to be introduced into a swine embryo, a step of mixing said expression transgenes is further added before step (b).

3. The method according to claim 1, wherein said transgenes are passed onto offspring throughbreeding.

4. The method according to claim 1, wherein each of said mammary gland specific promoter is bovine α-lactalbumin promoter.

5. The method according to claim 1, wherein the production and secretion of porcine lactoferrin on the mammary tissue of said swine act as an immune modulator, which can help boost the immunity and resistance of nursing offspring, reducing their diarrhea condition and fighting inflammation.

6. The method according to claim 1, wherein said production and secretion of hFIX and porcine lectoferrin on the mammary tissue of said swine last stably over lactation.

7. The method according to claim 1, wherein after step (d), further comprise the steps of:
   (e) collecting milk from said transgenic swine; and
   (f) isolating hFIX and porcine lactoferrin from said milk.

8. A method for producing a transgenic swine whose somatic and germ cells comprise transgenes, comprising the steps of:
   (a) constructing (i) an expression plasmid that comprises two transgenes wherein DNA sequences of said transgenes encode human clotting factor IX (hFIX) and porcine lactoferrin, respectively, wherein both transgenes are operably linked to a mammary gland specific promoter, or (ii) two expression transgenes, wherein one comprises a DNA sequence of transgene encoding human clotting factor IX (hFIX) operably linked to a mammary gland specific promoter, the other comprises a DNA sequence encoding porcine lactoferrin operably linked to a mammary gland specific promoter and the ratio of said two expression transgenes is 1:1;

(b) transferring said expression plasmid or transgenes into a swine embryo by gene injection;

(c) transplanting said embryo comprising said expression transgene or transgenes into a recipient; and (d) allowing said embryo to develop into a transgenic swine, wherein expression of said transgenes result in the production and secretion of hFIX and porcine lactoferrin on the mammary tissue of said swine.

9. The method according to claim 8, wherein when two expression transgenes are to be introduced into a swine embryo, a step of mixing said expression transgenes is further added before step (b).

10. The method according to claim 8, wherein said transgenes are passed onto offspring through breeding.

11. The method according to claim 8, wherein each of said of mammary gland specific promoter is bovine α-lactalbumin promoter.

12. The method according to claim 8, wherein the production and secretion of porcine lactoferrin on the mammary tissue of said swine act as an immune modulator, which can help boost the immunity and resistance of nursing offspring, reducing their diarrhea condition and fighting inflammation.

13. The method according to claim 8, wherein said production and secretion of hFIX and porcine lectoferrin on the mammary tissue of said swine last stably over lactation.

14. The method according to claim 8, wherein after step (d), further comprise the steps of:

(e) collecting milk from said transgenic swine; and (f) isolating hFIX and porcine lactoferrin from said milk.

* * * * *